US010952540B2

(12) United States Patent
Wiggermann

(10) Patent No.: US 10,952,540 B2
(45) Date of Patent: Mar. 23, 2021

(54) ADAPTABLE MATTRESS HAVING A PHASE CHANGEABLE COMPONENT WITH LATICES AND SPRING ELEMENTS

(71) Applicant: Hill-Rom Services, Inc., Batesville, IN (US)

(72) Inventor: Neal Wiggermann, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/688,216

(22) Filed: Nov. 19, 2019

(65) Prior Publication Data

US 2020/0085204 A1 Mar. 19, 2020

Related U.S. Application Data

(62) Division of application No. 15/604,933, filed on May 25, 2017, now abandoned.

(Continued)

(51) Int. Cl.

| | |
|---|---|
| ***A61F 7/02*** | (2006.01) |
| ***A47C 27/14*** | (2006.01) |
| ***A47C 27/15*** | (2006.01) |
| ***A47C 27/20*** | (2006.01) |
| ***A61G 7/00*** | (2006.01) |
| ***A61G 7/057*** | (2006.01) |

(52) U.S. Cl.

CPC ............ *A47C 27/148* (2013.01); *A47C 27/15* (2013.01); *A47C 27/20* (2013.01); *A61G 7/00* (2013.01); *A61G 7/057* (2013.01); *A61G 7/05715* (2013.01); *A61G 7/05738* (2013.01); *A61G 2203/34* (2013.01); *A61G 2210/90* (2013.01)

(58) Field of Classification Search

CPC ......... A61F 7/02; A47C 21/048; A47C 27/14; A47C 27/148; A47C 27/15; A47C 27/061

See application file for complete search history.

(56) References Cited

U.S. PATENT DOCUMENTS 3,202,801 A * 8/1965 Saluri .................... H05B 3/342 219/528

3,281,578 A * 10/1966 Chapman, Jr. .......... B22F 7/062 219/528

(Continued)

OTHER PUBLICATIONS

Macromolecular Materials and Engineering; Thermally Tunable, Self-Healing Composites for Soft Robotic Applications; 2014; Nadia G. Cheng, Arvind Gopinath, Oifeng Wang, Karl Iagnemma, Anette E. Hosoi; pp. 1279-1284.

(Continued)

*Primary Examiner* — Peter M. Cuomo
*Assistant Examiner* — Ifeolu A Adeboyejo
(74) *Attorney, Agent, or Firm* — Price Heneveld LLP

(57) ABSTRACT

A mattress includes a first, phase changeable component and a thermal management system adapted to control the temperature of the phase changeable component in order to change the firmness of the mattress. In one embodiment the phase changeable component includes two dimensional lattices separated from each other and a spring element extending between the lattices. Some embodiments of the mattress include an optional single phase component. The firmness can be made spatially and/or temporally uniform or nonuniform, and can be controlled based on one or more sensed parameters.

20 Claims, 17 Drawing Sheets

Related U.S. Application Data

(60) Provisional application No. 62/491,457, filed on Apr. 28, 2017.

(56) References Cited

U.S. PATENT DOCUMENTS

| | | | | | |
|---|---|---|---|---|---|
| 3,823,429 | A * | 7/1974 | Ambrose | A47C 7/342 | 267/84 |
| 4,278,869 | A * | 7/1981 | McMullan | A47C 27/085 | 219/217 |
| 5,020,176 | A * | 6/1991 | Dotson | A47C 27/082 | 137/487.5 |
| 5,092,008 | A * | 3/1992 | Okubo | A47C 27/005 | 5/484 |
| 5,329,096 | A * | 7/1994 | Suematsu | A47C 21/048 | 219/528 |
| 5,329,656 | A * | 7/1994 | Leggett | A47C 27/084 | 5/420 |
| 5,438,723 | A * | 8/1995 | Carroll | A47C 19/122 | 16/267 |
| 5,444,878 | A * | 8/1995 | Kang | A47C 21/048 | 5/421 |
| 5,626,657 | A * | 5/1997 | Pearce | A43B 5/0405 | 106/122 |
| 5,787,525 | A * | 8/1998 | Sugihara | A47C 31/00 | 5/421 |
| 5,835,983 | A * | 11/1998 | McMahen | A61F 7/007 | 219/527 |
| 5,881,409 | A * | 3/1999 | Pearce | A43B 5/0405 | 5/654 |
| 5,892,202 | A * | 4/1999 | Baldwin | A47J 36/2483 | 219/387 |
| 5,932,129 | A * | 8/1999 | Hyatt | F28D 20/028 | 219/528 |
| 5,966,763 | A * | 10/1999 | Thomas | A47C 27/086 | 5/715 |
| 6,018,143 | A * | 1/2000 | Check | A47J 47/145 | 219/387 |
| 6,026,527 | A * | 2/2000 | Pearce | C08L 51/006 | 5/654 |
| 6,121,578 | A * | 9/2000 | Owens | A47J 47/145 | 219/385 |
| 6,313,438 | B1 * | 11/2001 | Emerick, Jr. | H02S 20/10 | 219/212 |
| 6,378,948 | B1 * | 4/2002 | Macher | A47C 7/425 | 297/180.12 |
| 6,447,865 | B1 * | 9/2002 | Flick | B32B 25/04 | 428/52 |
| 6,598,251 | B2 | 7/2003 | Habboub et al. | | |
| 6,653,363 | B1 * | 11/2003 | Tursi, Jr. | C08G 18/7607 | 521/174 |
| 6,723,967 | B2 * | 4/2004 | Rock | A41D 13/0051 | 219/528 |
| 6,745,420 | B2 | 6/2004 | Giori et al. | | |
| 6,936,791 | B1 * | 8/2005 | Baldwin | A47J 36/2483 | 219/387 |
| 7,114,783 | B2 * | 10/2006 | Warren | A47C 4/54 | 297/452.41 |
| 7,930,782 | B2 * | 4/2011 | Chen | C08L 53/02 | 5/655.5 |
| 8,499,389 | B2 * | 8/2013 | Kirchhoff | A47C 31/123 | 5/697 |
| 8,956,715 | B2 * | 2/2015 | Kim | B32B 5/18 | 428/201 |
| 9,119,479 | B2 * | 9/2015 | Mikkelsen | A47C 21/048 | |
| 9,980,578 | B2 * | 5/2018 | Mikkelsen | A47C 21/042 | |
| 10,104,983 | B1 * | 10/2018 | Robins | A47C 31/105 | |
| 2002/0078509 | A1 * | 6/2002 | Williams | A47C 27/148 | 5/716 |
| 2003/0109908 | A1 * | 6/2003 | Lachenbruch | A47C 27/148 | 607/96 |
| 2004/0074008 | A1 * | 4/2004 | Martens | A47C 23/068 | 5/740 |
| 2004/0112891 | A1 * | 6/2004 | Ellis | A61F 7/007 | 219/528 |
| 2006/0151459 | A1 * | 7/2006 | Ku | A47C 27/088 | 219/217 |
| 2008/0216231 | A1 * | 9/2008 | Lambarth | A61G 7/1026 | 5/81.1 HS |
| 2009/0188048 | A1 * | 7/2009 | Shlomo | A47C 21/046 | 5/691 |
| 2009/0217458 | A1 * | 9/2009 | Lord | A47D 15/008 | 5/655 |
| 2009/0288259 | A1 * | 11/2009 | Lean | B29C 44/22 | 5/740 |
| 2010/0005594 | A1 * | 1/2010 | Rancourt | A47C 27/146 | 5/652 |
| 2010/0194171 | A1 * | 8/2010 | Hirata | B60N 2/01508 | 297/452.48 |
| 2011/0000018 | A1 * | 1/2011 | Kirchhoff | A47C 31/123 | 5/421 |
| 2011/0252562 | A1 * | 10/2011 | Mikkelsen | A47C 21/048 | 5/421 |
| 2011/0289683 | A1 * | 12/2011 | Mikkelsen | A61F 7/02 | 5/421 |
| 2012/0222216 | A1 * | 9/2012 | Jin | A47C 19/122 | 5/400 |
| 2012/0284928 | A1 * | 11/2012 | Henderson | A47C 27/053 | 5/717 |
| 2013/0074270 | A1 * | 3/2013 | Caruso | A47C 31/08 | 5/658 |
| 2014/0165292 | A1 | 6/2014 | Gladne | | |
| 2014/0189951 | A1 * | 7/2014 | DeFranks | A47C 27/064 | 5/423 |
| 2014/0208517 | A1 * | 7/2014 | Gross | A47C 27/085 | 5/591 |
| 2014/0325758 | A1 * | 11/2014 | Mikkelsen | A47C 21/042 | 5/421 |
| 2015/0040327 | A1 * | 2/2015 | Mikkelsen | A47C 27/15 | 5/740 |
| 2015/0067967 | A1 | 3/2015 | Tyree | | |
| 2015/0289667 | A1 * | 10/2015 | Oakhill | A47C 21/044 | 5/423 |
| 2015/0308533 | A1 * | 10/2015 | DeFranks | A47C 7/22 | 5/690 |
| 2015/0320226 | A1 * | 11/2015 | Mikkelsen | A61F 7/02 | 5/421 |

OTHER PUBLICATIONS

Squishy robots MIT News on Campus and around the World; Phase-changing material could allow even low-cost robots to switch between hard and soft states.; Cambridge, MA; Helen Knight; MIT News correspondent Jul. 14, 2014.

* cited by examiner

ADAPTABLE MATTRESS HAVING A PHASE CHANGEABLE COMPONENT WITH LATICES AND SPRING ELEMENTS

CROSS REFERENCE TO RELATED APPLICATIONS

This is a Divisional of U.S. application Ser. No. 15/604,933 filed on May 25, 2017 and entitled "Adaptable Mattress", which claims priority to U.S. Provisional Application 62/491,457 filed Apr. 28, 2017 and entitled "Adaptable Mattress", the contents of which are incorporated herein by reference. The Aug. 2, 2017 amendment of paragraphs 0040, 0042 and 0047, and the Aug. 7, 2019 amendment of paragraphs 0020, 0026, 0027 and FIG. 1C of drawing sheet 1 of application Ser. No. 15/604,933 are incorporated in this Divisional application.

TECHNICAL FIELD

The subject matter described herein relates to mattresses and particularly to a mattress which is adaptable to accommodate occupants with diverse support requirements.

BACKGROUND

A mattress used on a beds in a health care setting should provide comfort for a wide variety of patient sizes, weights, and morphologies. The mattress should also minimize the risk that the patient will develop pressure ulcers, irrespective of his size, weight, and morphology.

Consider, for example, the weight range from a very light weight patient to a very heavy weight patient. It is desirable for both the light patient and the heavy patient to sink far enough into the mattress to maximize, as much as possible, the contact area between the patient and the mattress. The maximized contact area reduces both the overall mattress/patient interface pressure and the likelihood of local regions of high interface pressure. The reduced interface pressure mitigates the possibility that the patient will develop pressure ulcers and may also contribute to improved patient comfort.

A relatively firm mattress may be more satisfactory than a soft mattress for a heavy patient. The heavy patient will sink (become immersed) deep enough into a firm mattress to experience a large contact area and therefore low interface pressure and good comfort, but not so far that he bottoms out on the underlying frame. Bottoming out on the frame, like insufficient immersion, can cause localized pressure concentrations on the patient's body which can contribute to the likelihood of pressure ulcer development.

Conversely, a relatively soft mattress may be more suitable for a light weight patient. Because of his light weight the patient will be inherently less likely to bottom out on the bed frame despite the softness of the mattress. In addition, if the light weight patient were on a mattress firm enough for the heavy patient, he would experience insufficient immersion, and therefore elevated pressure ulcer risk.

One way to accommodate the diverse requirements of heavy patients and light weight patients is to employ a mattress comprised of multiple bladders which are designed to be operated at various internal pressures to suit the needs of specific patients. The bladders are pressurized with air to a relatively high pressure to bear the weight of a heavy patient and are pressurized more modestly for the light patient. Mattresses which include pressurizable bladders also have the advantage of being operable in one or more therapy delivery modes. One example is a continuous lateral rotation mode in which air pressure in the bladders is varied cyclically so that the pressure amplitude cycles on the left and right sides of the mattress are out of phase with each other.

However pressurizable mattresses, despite their many merits, are not without drawbacks. Pressurizable mattresses have numerous components such as valves, solenoids, relays, blowers and air conduits which make them complex and costly. In addition, the components can generate undesirable noise when operated. Although the noise may be tolerable during occasional adjustments of bladder pressure, the persistent noise associated with more continuous operation, such as the continuous rotation therapy mode described above, may be objectionable. For example the continuous noise can disturb the sleep of the patient occupying the mattress and that of nearby patients.

What is needed is a mattress whose firmness is adjustable to meet the needs of a variety of patients, that operates with little or no noise, and which can be manufactured at low cost with relatively simple components.

SUMMARY

A mattress disclosed herein includes a first, phase changeable component and a thermal management system. The thermal management system is adapted to control the temperature of the phase changeable component thereby changing the stiffness or firmness of the mattress.

BRIEF DESCRIPTION OF THE DRAWINGS

The foregoing and other features of the various embodiments of the mattress described herein will become more apparent from the following detailed description and the accompanying drawings in which.

DETAILED DESCRIPTION

Figure 1A:
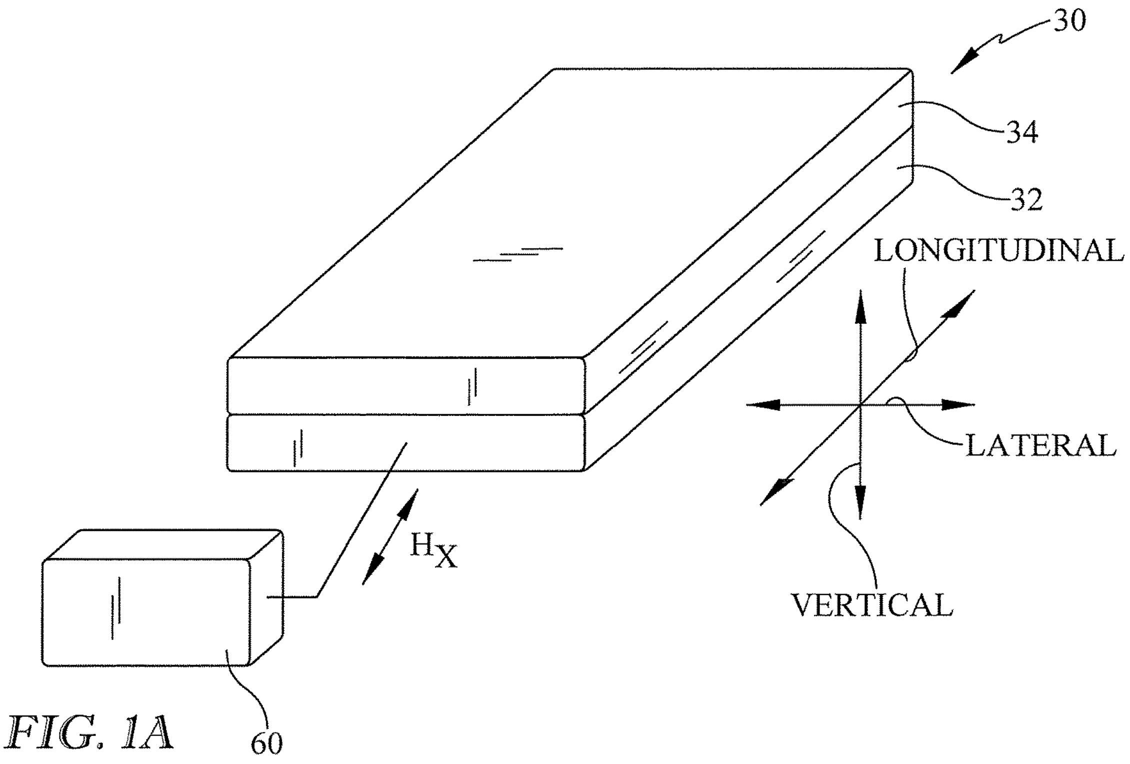
FIG. 1A is a perspective view of a mattress showing a phase changeable component, an optional single phase component vertically above the phase changeable component and a thermal management system.

Reference will now be made to embodiments of the invention, examples of which are illustrated in the accompanying drawings. Features similar to or the same as features already described may be identified by the same reference numerals already used. The terms "substantially" and "about" may be used herein to represent the inherent degree of uncertainty that may be attributed to any quantitative comparison, value, measurement or other representation. These terms are also used herein to represent the degree by which a quantitative representation may vary from a stated reference without resulting in a change in the basic function of the subject matter at issue.

Figure 1B:
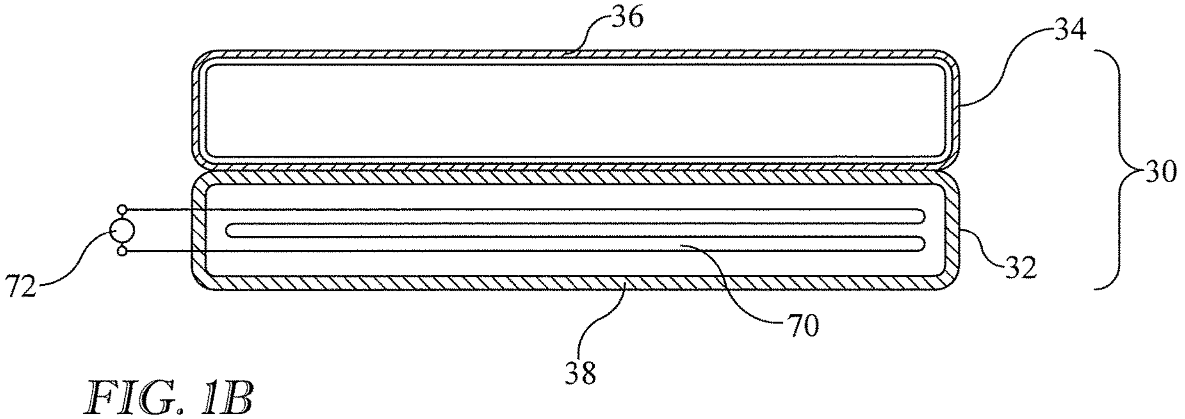
FIG. 1B is a side elevation view of the mattress of FIG. 1.
Figure 1C:
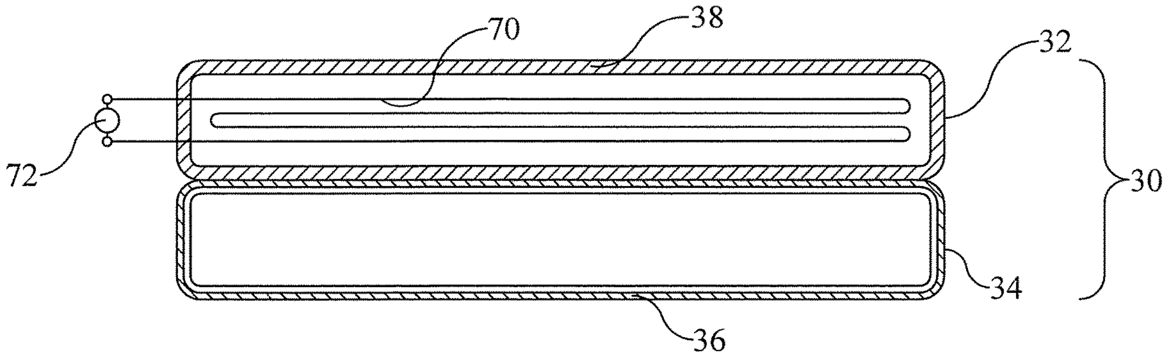
FIG. 1C is a side elevation view of a mattress similar to that of FIG. 1B but with the optional single phase component vertically below the phase changeable component.

Referring to FIGS. 1A-1C, mattress 30 includes a first component 32 and an optional second component 34. The first component 32 is a phase changeable component. As used herein, "phase changeable component" refers to a wax coated or wax infused cellular solid "backbone". The component is referred to as a phase changeable component because, as described in more detail below, the wax can be warmed to a liquid state or cooled to a solid state to affect the stiffness or firmness of the mattress.

Example backbones include disordered random skeletons, reticulated structures and ordered lattice structures. One specific example backbone is polyurethane foam. Another specific example is a three dimensional (3D) printed lattice made from a UV-curable flexible acrylic.

The wax coating or infused wax is the thermally active element of the phase changeable component. Wax is selected as the thermally active component because of its wetting properties, i.e. its ability to maintain contact, when liquid, with a wide spectrum of solid surfaces, and because many waxes transition between solid and liquid states at relatively low temperatures, allowing energy efficient transformations between morphable and rigid configurations. A specific example is batik wax.

Further details of such phase changeable components can be found in "Thermally Tunable, Self-Healing Composites for Soft Robotic Applications", authored by Nadia G. Cheng, Arvind Gopinath, Lifeng Wang, Karl Iagnemma, and Anette E. Hosoi, and appearing in Macromolecular Materials and Engineering 2014, 299, 1279-1284, the contents of which are incorporated herein by reference. The cited paper is referred to hereinafter as "Cheng, et al.". Specific embodiments of phase changeable components and mattresses employing phase changeable components are also described later in this specification.

Figure 2A:
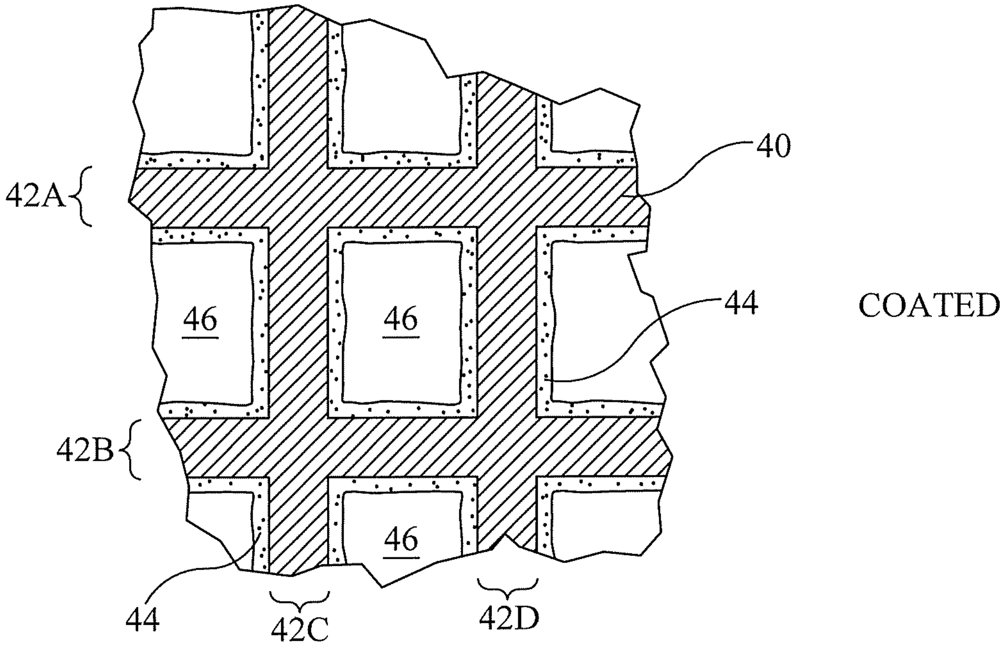
FIG. 2A is a schematic cross sectional view of a phase changeable component comprised of a backbone lattice coated with solid phase wax.

FIG. 2A is a schematic illustration of a cross section of a wax coated lattice backbone 40 comprised of ribs 42. Solid phase wax 44 covers the ribs of the lattice but does not completely or substantially completely occupy the inter-rib spaces 46.

Figure 2B:
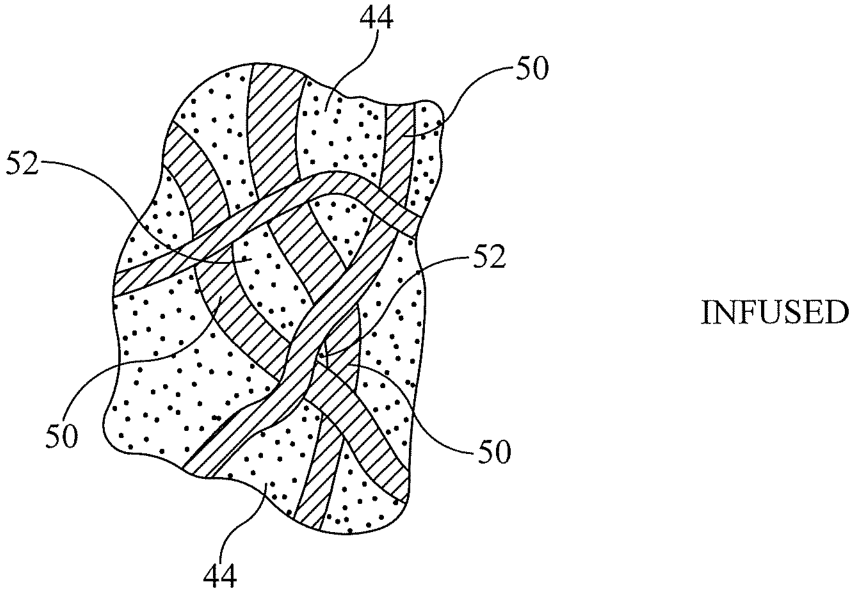
FIG. 2B is a schematic cross sectional view of a phase changeable component comprised of a reticulated backbone infused with solid phase wax.

FIG. 2B is a schematic illustration of a cross section of a wax infused reticulated backbone comprised of strands 50 of the backbone material. Solid phase wax 44 covers the strands 50 of the reticulated backbone material and also bridges across and completely or substantially completely occupies the interstices 52 defined by the strands.

The optional second component is a single phase component. The second component is referred to as "single phase" because, unlike the phase changeable component, it does not change phase during normal operation or contain any constituents that change phase during normal operation. One example of a single phase component is a component made of a polyurethane foam. One relevant definition of foam is a material in a lightweight cellular spongy form. Another definition of foam is a substance in which air or gas bubbles are trapped inside a solid or liquid. The "or liquid" portion of the immediately preceding definition is inapplicable to the mattress disclosed herein. As seen in FIGS. 1B and 1C the single phase component may be enclosed in or partially covered by a ticking 36.

The mattress also includes a thermal management system 60 adapted to control the temperature of the phase changeable component in order to control the firmness of the mattress. As used herein, the temperature of the phase changeable component means the temperature of wax 44, even if other constituents of the phase changeable component, such as backbone 40, may be at a temperature different than that of the wax due to, for example, differences in the heat capacities of the wax and the backbone. Accordingly, "temperature of the phase changeable component" and similar phrases are used synonymously with "temperature of the wax" and similar phrases.

Controlling the temperature of a phase changeable component enables the phase changeable component, and therefore the mattress, to transition between a firmer state in which the phase changeable component is relatively more rigid and a softer state in which the phase changeable component is relatively more flexible. In particular, the phase changeable component is relatively firmer at lower temperature and relatively softer and more compliant at higher temperature. This is because when the phase changeable component is at the lower temperature, its stiffness is (or approximates) that of the solid state wax coating or infused wax. When enough heat is applied, the wax melts. The melted wax drips to the bottom of the phase changeable component and/or continues to adhere to the backbone. Because the backbone is no longer coated with solid state wax the firmness of the mattress is (or approximates) the stiffness of the backbone, which is relatively soft and compliant in comparison to the solid state wax coated backbone. The phase changeable component can be returned to the firm state by reducing the temperature of the phase changeable layer (specifically the temperature of the wax) enough to allow the wax to resolidify. To the extent that the wax had dripped to the bottom of the phase changeable component, the wax migrates upwardly and recoats or re-infuses the backbone before returning to its solid state.

One mechanism of the upward migration is capillary action. To the extent that the liquid phase wax continues to adhere to the backbone, no such migration is necessary. In practice some of the wax may drip to the bottom of the phase changeable component and some may continue to adhere to the backbone.

Firmness states intermediate the firm state (wax thoroughly solidified) and the soft state (wax melted) can be achieved by using a wax that softens over a range of temperature while remaining solid. As the temperature of the solid phase wax increases the phase changeable component becomes progressively softer. Conversely, as the temperature of the wax decreases the phase changeable component becomes progressively firmer.

In FIG. 1A the thermal management system 60 is illustrated schematically. In FIG. 1B the illustrated thermal management system comprises a wire resistance heating element 70 connected to a voltage source 72. The thermal management system is considered to be an active system because its operation requires energy input (electrical energy in the example of FIG. 1B) as distinct from, for example, a passive thermal insulator or thermal conductor.

As illustrated in FIGS. 1A-1C, the first, phase changeable component 32 and the second, single phase component 34, are vertically distinct first and second layers. FIGS. 1A and 1B show a mattress in which the single phase layer 34 is vertically above the phase changeable layer 32 when the mattress is oriented and used as intended by its manufacturer or designer. FIG. 1C shows an alternate embodiment in which the phase changeable layer 32 is above the single phase layer 34 when in the mattress is oriented and used as intended by its manufacturer or designer.

As seen in FIGS. 1A-1C the phase changeable layer includes a leak barrier 38 which contains the liquid phase wax.

Figure 3:
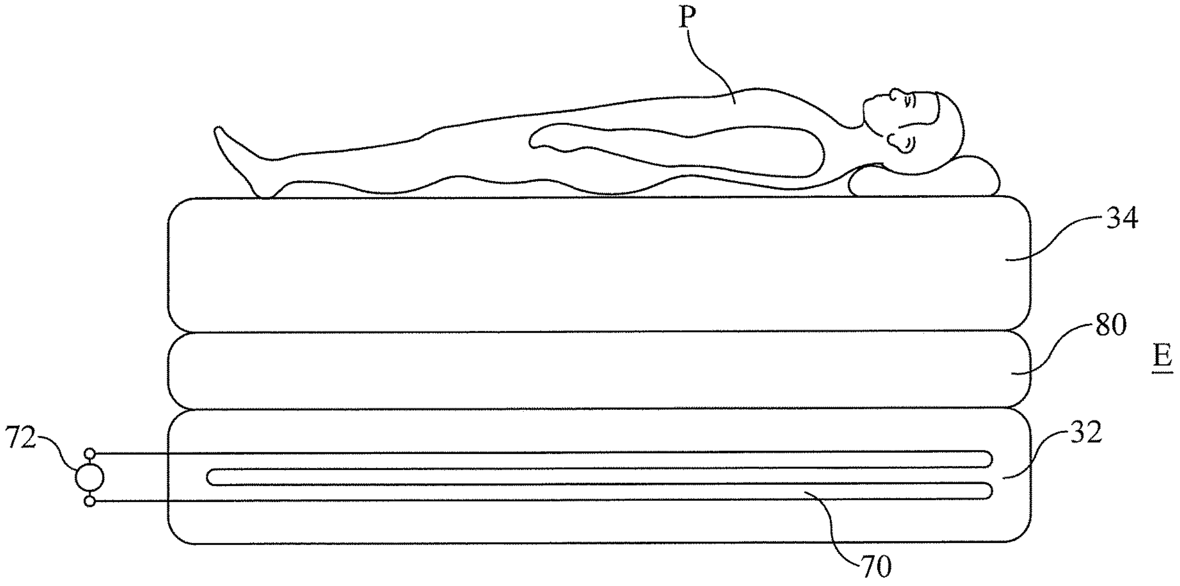
FIG. 3 is a side elevation view of a mattress similar to that of FIG. 1B including a thermal barrier between the single phase component and the phase changeable component.

FIG. 3 illustrates an embodiment similar to that of FIG. 1B but which also includes a thermal barrier 80 between the single phase layer and the phase changeable layer. The illustrated thermal barrier is a thermal barrier layer. The thermal barrier layer reduces heat transfer from the resistance heating element 70 to the patient P.

Figure 4:
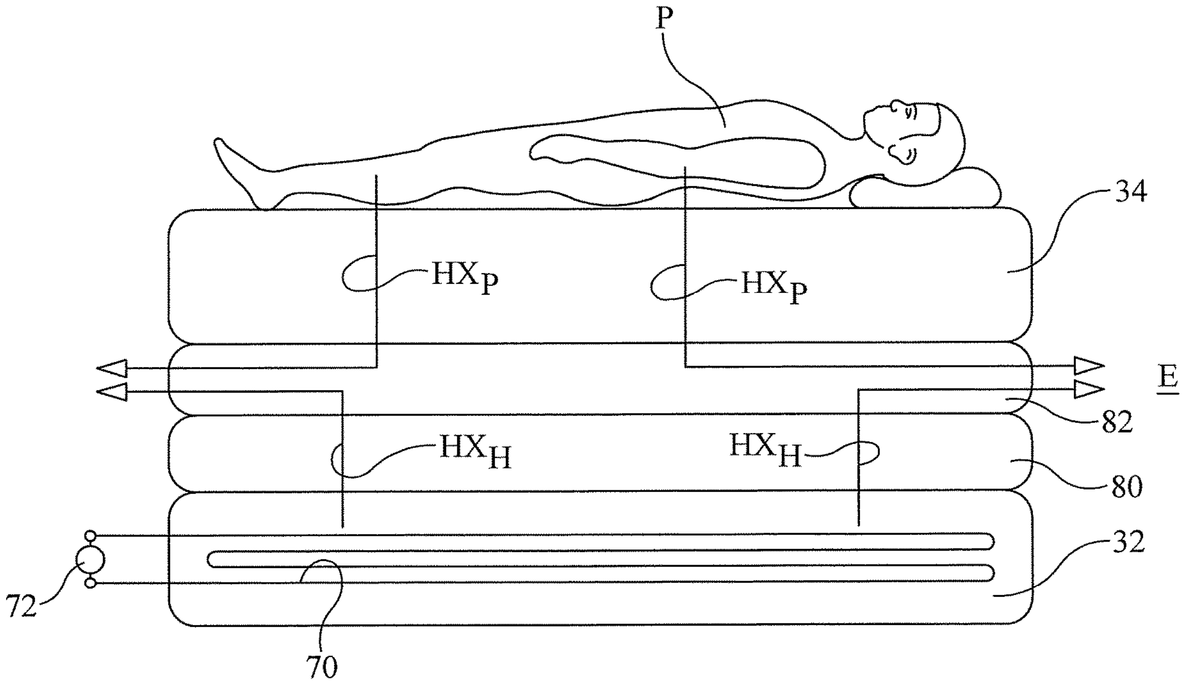
FIG. 4 is a side elevation view of a mattress similar to that of FIG. 3 but including a thermal conductor between the single phase component and the phase changeable component.

FIG. 4 illustrates an embodiment similar to that of FIG. 3 but which also includes a thermal conductor 82 between the single phase layer and the phase changeable layer. The illustrated thermal conductor is a thermal conductor layer. Although both the thermal barrier 80 and thermal conductor 82 are between the first and second components or layers, the thermal barrier is closer to the phase changeable layer 32 and the thermal conductor is closer to the single phase layer 34. The thermal conductor layer absorbs heat which passes vertically through the thermal barrier as a result of the thermal barrier being less than 100% effective, and conducts that heat to the local environment E as indicated by arrows $HX_H$. The thermal conductor layer may also conduct body heat from the occupant to environment E as indicated by arrows $HX_P$.

In FIGS. 1B, 1C, 3, 4, and 5A the thermal management system 60 is a heat supply system 62, such as an electrical resistive heating element 70 and voltage source 72, adapted to supply heat to the phase changeable layer. In operation, heat supplied by way of the heat supply system raises the temperature of the phase changeable component thereby causing the phase changeable component to transition from its firmer, more rigid state to its softer, more compliant state. As a result, mattress 30 can accommodate both a heavy patient such as a bariatric patient, and a light weight patient. When the phase changeable component 32 is at a baseline temperature such as room temperature the phase changeable component is in its firm state, and the mattress is ready to accept the heavy patient. To prepare the mattress to receive a light patient, a caregiver operates the heat supply system to heat the phase changeable component, causing it to transition to a softer, more compliant state which is more suitable for the light weight patient.

Figure 5A:
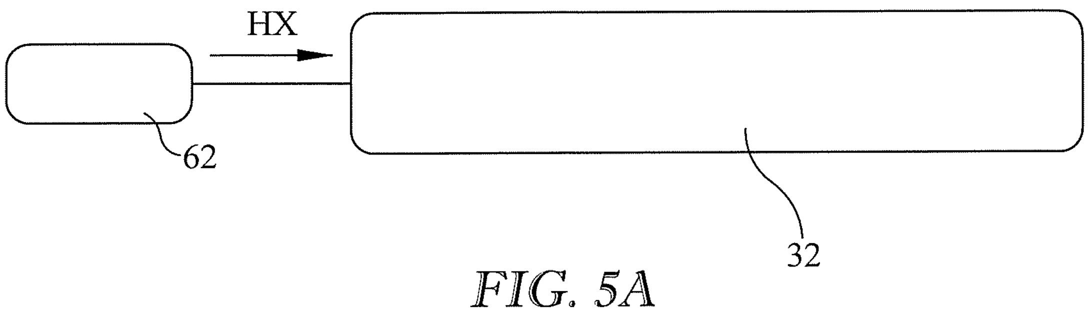
FIG. 5A is a schematic side elevation view of a phase changeable component and a thermal management system in the form of a heat supply system.
Figure 5B:
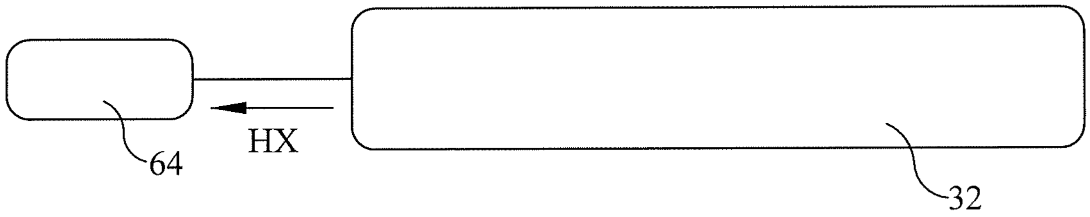
FIG. 5B is a schematic side elevation view of a phase changeable component and a thermal management system in the form of a heat withdrawal system.

FIG. 5B shows an embodiment similar to that of FIGS. 1B, 1C, 3, 4, and 5A but in which in thermal management system 60 is a heat withdrawal system 64 adapted to withdraw heat from the phase changeable layer. One example of a heat withdrawal system is a Peltier cooling device 90 (FIG. 7) (which is sometimes referred to as a thermoelectric device) adapted to withdraw heat from the phase changeable layer. In operation, heat withdrawn by way of the heat withdrawal system lowers the temperature of the phase changeable component thereby causing the phase changeable component to transition from a softer, more compliant state to a firmer, more rigid state. As a result, mattress 30 can accommodate both a heavy patient such as a bariatric patient, and a light weight patient. The heat withdrawal system may be used to accelerate the transition from the soft state to the firm state when an unoccupied mattress which was previously occupied by a light weight patient is being prepared to accept a heavy patient. As will become apparent from the discussion of FIGS. 10A-10E, below, it may be necessary to unload the phase changeable component in order to effect a transition from the soft state to the firm state. If so, the soft-to-firm transition may be carried out by sequentially unloading sections of the phase changeable component, then actively cooling the unloaded sections (or allowing them to cool naturally) so that they return to their firm state. A load can then be applied to the section.

When the phase changeable component is at a baseline temperature such as room temperature the phase changeable component is in its soft or compliant state, and the mattress is ready to accept the light weight patient.

To prepare the mattress to receive a heavy patient, a caregiver operates the heat withdrawal system to cool the phase changeable component, causing it to transition to the firmer state which is more suitable for the heavy patient. In another embodiment a control unit automatically turns on the heat withdrawal system if the patient is absent from the mattress for a long enough time to indicate that the bed should be prepared to receive a different patient, for example because the original patient has been discharged or moved to a different bed. Patient absence can be determined in any suitable way, for example by pressure sensors, weight sensors or analysis of a camera image by object recognition software. As already noted it may be necessary to remove weight from the phase changeable component in order to effect a transition from softer to firmer, but it is not necessary to remove weight from the phase changeable component in order to effect a transition from firmer to softer. As a result the firm state is believed to be the appropriate default state for an unoccupied mattress.

Figure 6:
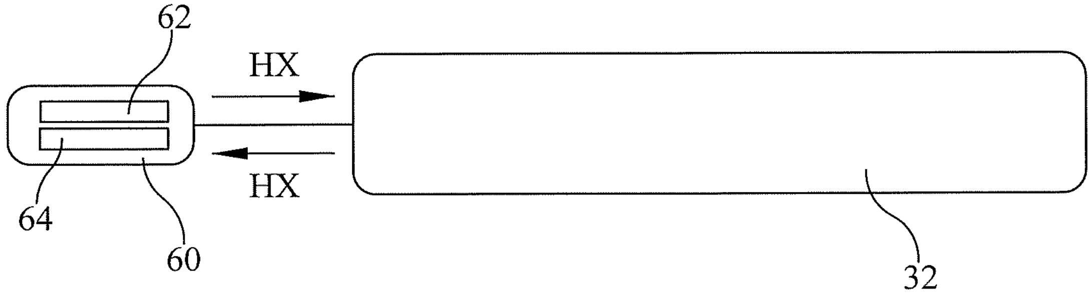
FIG. 6 is a schematic side elevation view similar to that of FIGS. 5A and 5B in which the thermal management system includes a heat supply system and a heat withdrawal system.

FIG. 6 shows an embodiment similar to that of FIGS. 1B-5B in which thermal management system 60 includes both a heat supply system 62 adapted to supply heat to the phase changeable component and a heat withdrawal system 64 adapted to withdraw heat from the phase changeable component.

Figure 7:
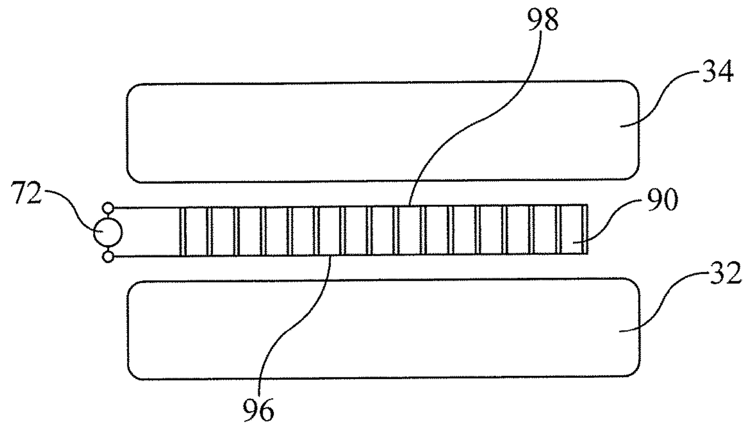
FIG. 7 is a schematic side elevation view of a mattress having a single phase component, a phase changeable component and a Peltier module between the single phase and phase changeable components.

FIG. 7 shows a mattress embodiment, which includes Peltier device or module 90. When electric current flows through the Peltier device, one side 96 of the device, which is referred to as the hot side, becomes warm. The other side 98, which is referred to as the cold side, becomes cool. The module is oriented so that its hot side 96 faces the phase changeable component 32 and its cold side 98 faces the single phase component. The hot side serves as a heat source that supplies heat to the phase changeable component and the cold side serves as a heat sink that receives excess heat from the single phase component, for example body heat from the patient. The polarity of the voltage to the Peltier device can be reversed so that side 96 is the cold side and side 98 is the hot side. The Peltier device can then be used to withdraw heat from the phase changeable component. Thus, the Peltier device can serve as a heater to apply heat to the phase changeable component and provoke a solid-to-liquid phase transition of the wax, and can also serve as a chiller to withdraw heat from the phase changeable layer and provoke a liquid-to-solid phase transition of the wax.

Figure 8A:
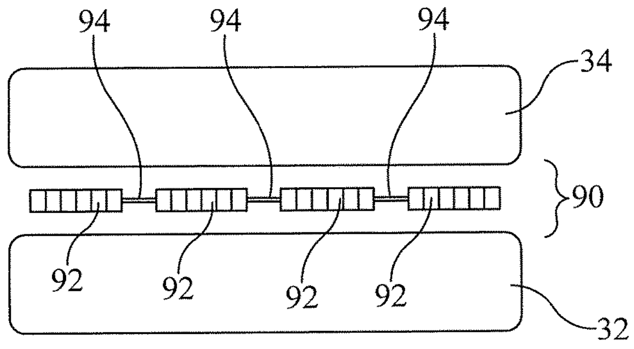
FIG. 8A is a schematic side elevation view similar to that of FIG. 7 in which the Peltier module is comprised of segments connected together by connectors.
Figure 8B:
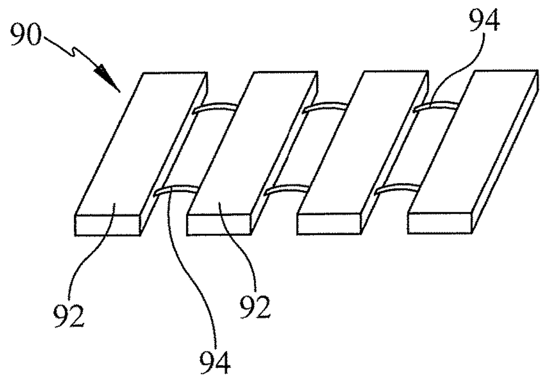
FIG. 8B is a perspective view of a Peltier module comprised of longitudinally distributed segments connected together by connectors.
Figure 8C:
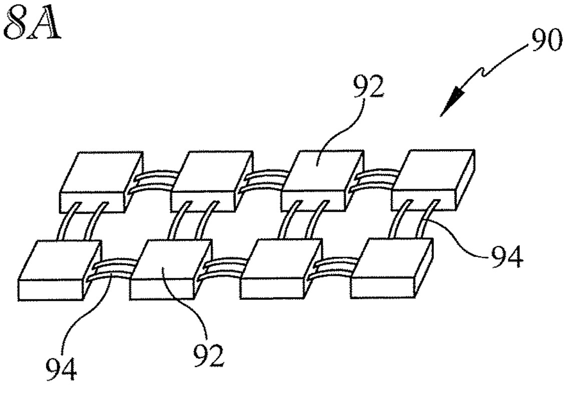
FIG. 8C is a perspective view of a Peltier module comprised of longitudinally and laterally distributed segments connected together by connectors.

FIGS. 8A-8C show embodiments similar to that of FIG. 7 except that the Peltier device comprises two or more Peltier segments 92 connected together by connectors 94 which give each segment some independence of motion relative to the other segments. The segmented design of FIGS. 8A-8C may conform more closely to the patient's body than does the unsegmented embodiment of FIG. 7. The segmentation may be one-way segmentation, such as longitudinal segmentation (FIG. 8B) or lateral segmentation (not illustrated), or may be two-way segmentation (FIG. 8C).

Figure 9:
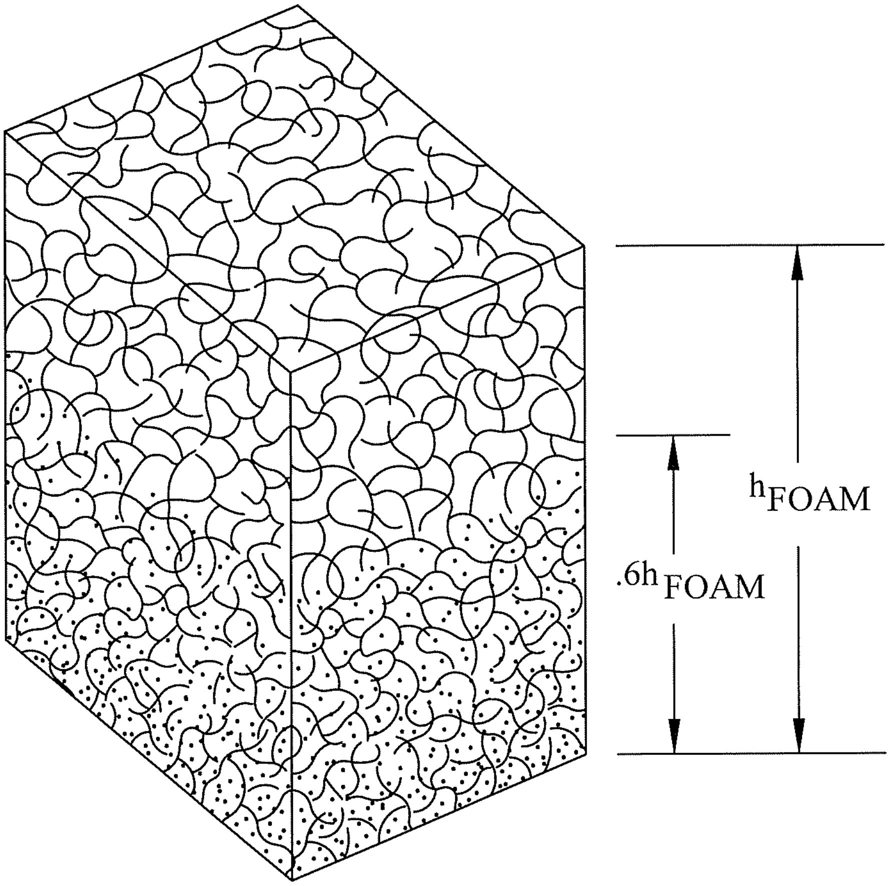
FIG. 9 is a perspective view of a portion of a phase changeable component in the form of a wax infused open cell foam.

Example architectures of the phase changeable component are the wax coated lattice backbone of FIG. 2A and the wax infused reticulated mesh of FIG. 2B, both illustrated in their firm state in which the wax is in the solid phase. Another example of a phase changeable architecture is a wax infused foam, for example the open cell foam of FIG. 9. In the sample of FIG. 9 the foam has a maximum height $h_{FOAM}$. The density of the solid state wax decreases with increasing height h, i.e. from h=0 to h=0.6 $h_{FOAM}$ because during the liquid-to-solid transition the wax did not reinfuse the foam above approximately 0.6 $h_{FOAM}$.

FIGS. 10A-10E are views of another phase changeable architecture which includes two or more vertically separated two dimensional (2D) lattices 100 with springs elements 102 extending between the lattices. In the illustrated embodiment the spring elements are arcuate filaments.

Figure 10A:
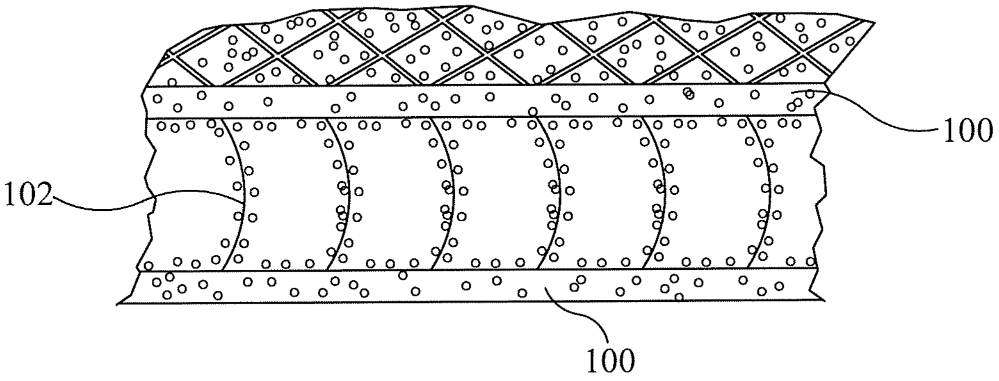
FIG. 10A is a perspective view of a portion of a phase changeable component which includes two vertically separated two dimensional lattices with spring elements extending between the lattices.
Figure 10B:
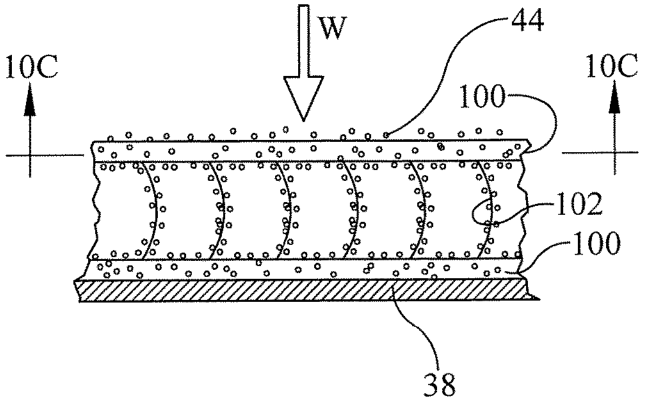
FIG. 10B is a side elevation view of the phase changeable component of FIG. 10A with a weight applied to the component and with the component shown in a firm state.
Figure 10C:
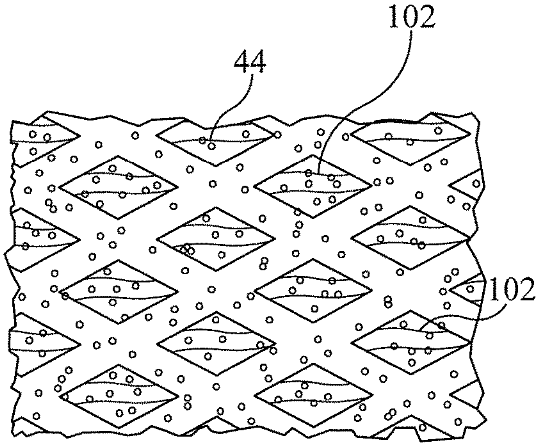
FIG. 10C is a view taken in the direction 10C-10C of FIG. 10B.

FIGS. 10A-10C show the phase changeable component in its firm state. As seen best in FIG. 10B, when the component is in its firm state solid phase wax 44 coats the lattices and filaments so that the stiffness of the phase changeable component corresponds to the stiffness of the wax coated filaments.

Figure 10D:
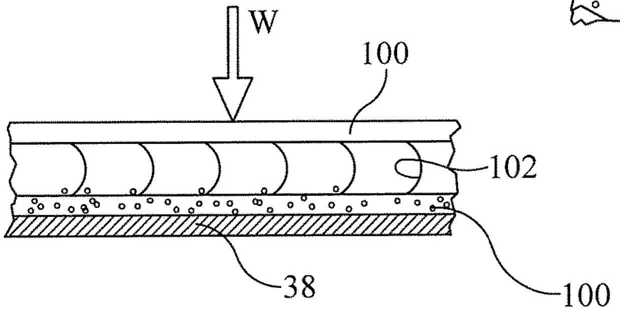
FIG. 10D is a side elevation view of the phase changeable component of FIG. 10A with a weight applied to the component and with the component shown in a soft state.

As seen in FIG. 10D, when the temperature of the phase changeable component is increased sufficiently, the wax melts and drips to the bottom of the component as illustrated and/or continues to adhere to the filaments (not illustrated). To the extent that the wax continues to adhere to the filaments, the fact that the wax is in its liquid phase causes it to not contribute to the stiffness of the phase changeable component. (For this reason, even though liquid phase wax may cling to the backbone, the backbone is not considered to be coated in the same sense that "coated" is applied to the backbone when covered with solid phase wax.) Instead, the stiffness of the phase changeable component corresponds to the stiffness of the filaments themselves, which is less than the stiffness of the solid wax coated filaments. Weight W causes the uncoated filaments to undergo additional flexure as seen by comparing FIG. 10D to FIG. 10B.

Figure 10E:
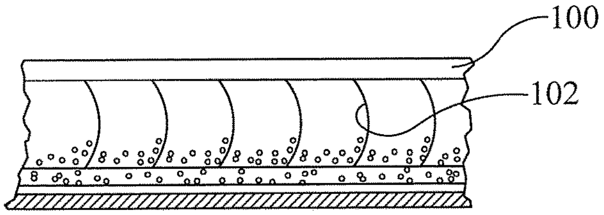
FIG. 10E is a side elevation view of the phase changeable component of FIG. 10A with no weight applied to the component and with the component shown in a state of transition from the soft state to the firm state.

FIG. 10E shows the phase changeable component during transition from the soft state of FIG. 10D to the firm state of FIG. 10B. In FIG. 10E weight W has been removed from the phase changeable component, allowing the filaments to spring back to the less flexed state of FIG. 10B. To the extent that the liquid wax pooled at the bottom of the component (as seen in FIG. 10D) rather than adhering to the filaments, liquid wax migrates up the filaments, for example due to capillary action. As the wax cools and re-solidifies, the phase changeable component returns to the state seen in FIG. 10B. To the extent that the liquid phase wax continued to adhere to the backbone, migration up the filaments is not necessary.

As is evident from the foregoing explanation, allowing the backbone of the phase changeable component to spring back to its unloaded state while the wax is still in its liquid phase may be a precondition for enabling the transition of the phase changeable component from the soft state (FIG. 10D) to the firm state (FIG. 10B). One way this can be accomplished is by removing the weight W.

Figure 11:
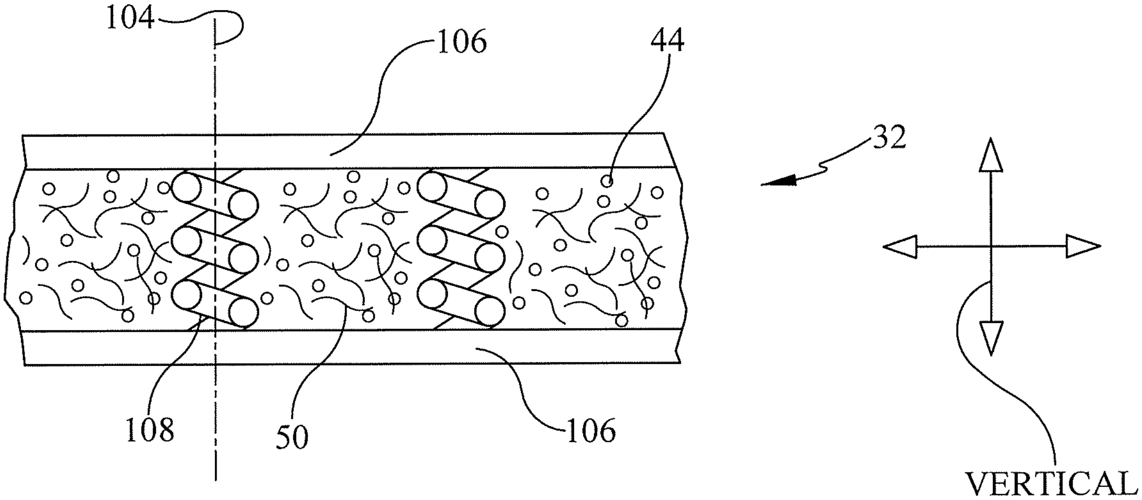
FIG. 11 is a cross sectional elevation view of a portion of a phase changeable component showing springs for resisting development of a permanent compression set in the component.

FIG. 11 is a cross sectional elevation view of a portion of a phase changeable component 32 in its firm state. The component includes strands 50 of a reticulated mesh and solid state wax 44 between backing sheets 106. One or more springs or spring-like elements 108 extend between the backing sheets, i.e. with spring axis 104 oriented vertically. The springs help the phase changeable component resist the development of a permanent compression set in the vertical direction. Springs or spring-like elements may also be used with their axes oriented horizontally in order to resist compression set in the lateral and/or longitudinal directions.

Figure 12A:
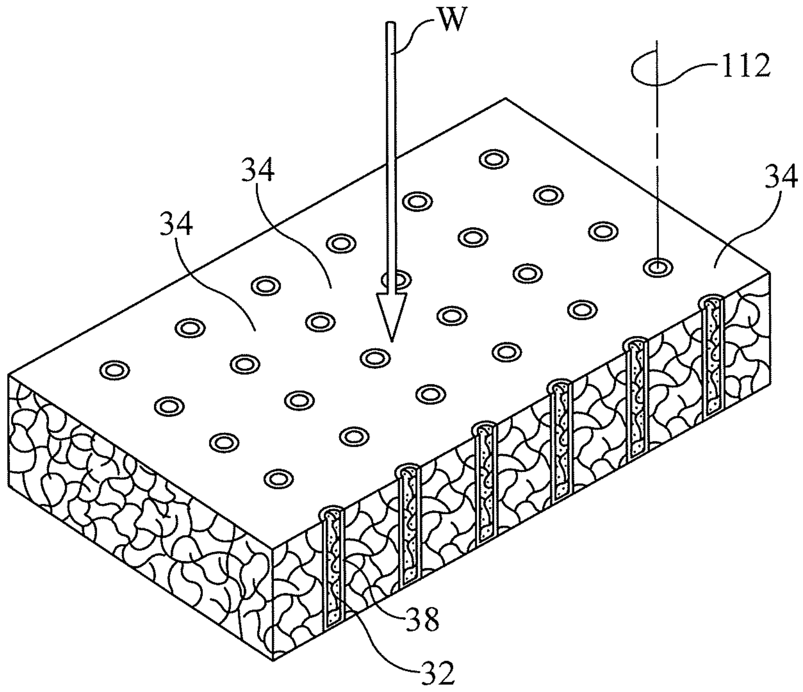
FIGS. 12A, 12B, and 12C are views of a mattress architecture comprised of a single phase component and a phase changeable component in the form of pedestals which are vertically coextensive with the single phase component and which are separated from the single phase component by a leak barrier.
Figure 12B:
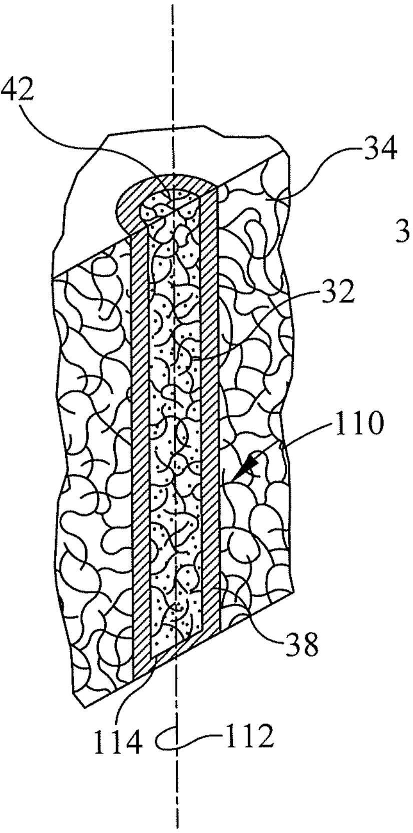
Figure 12C:
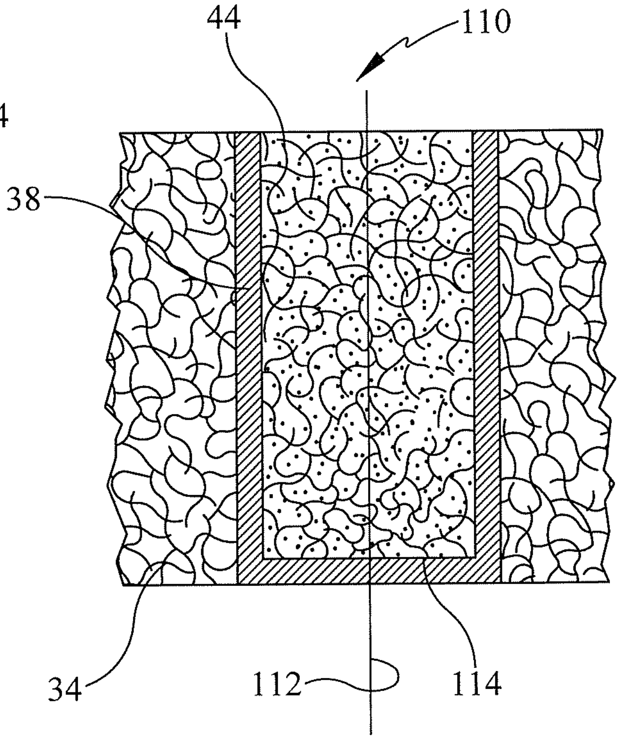

FIGS. 12A-12C show a mattress architecture in which the phase changeable component 32 and the single phase component 34 are vertically coextensive. In the example of FIGS. 12A-12C the single phase component comprises a conventional polyurethane foam, and the phase changeable component is an array of pedestals 110 comprised of a wax coated or wax infused backbone. In the example of FIG. 12 the backbone of the phase changeable component is the same polyurethane foam used to construct the single phase component. The phase changeable pedestals are uniformly distributed in the single phase foam layer with their longitudinal axes 112 parallel to the mattress load bearing direction, which is illustrated as the patient's weight vector W.

The mattress also includes a containment or leak barrier 38 for each pedestal. Each leak barrier may be considered to be an element of the single phase layer or an element of the phase changeable layer. Each leak barrier is comprised of a material impermeable to liquid wax. Each leak barrier circumscribes its pedestal, extends across the bottom 114 of the pedestal and may also extend across the top of the pedestal. At a high temperature at which the wax is softened or liquified, the containment barrier prevents wax from 1) leaking out of the bottom of the phase changeable layer (which is coplanar with the bottom of the single phase layer) or 2) being drawn into the foam of the single phase layer (e.g. by capillary action). At the higher temperature the firmness of the mattress is (or approximates) the stiffness of the foam. At a lower temperature at which the wax is solid and has re-infused the foam constituent of the pedestal, the firmness of the mattress depends on the stiffness of the wax infused pedestals.

Figure 13:
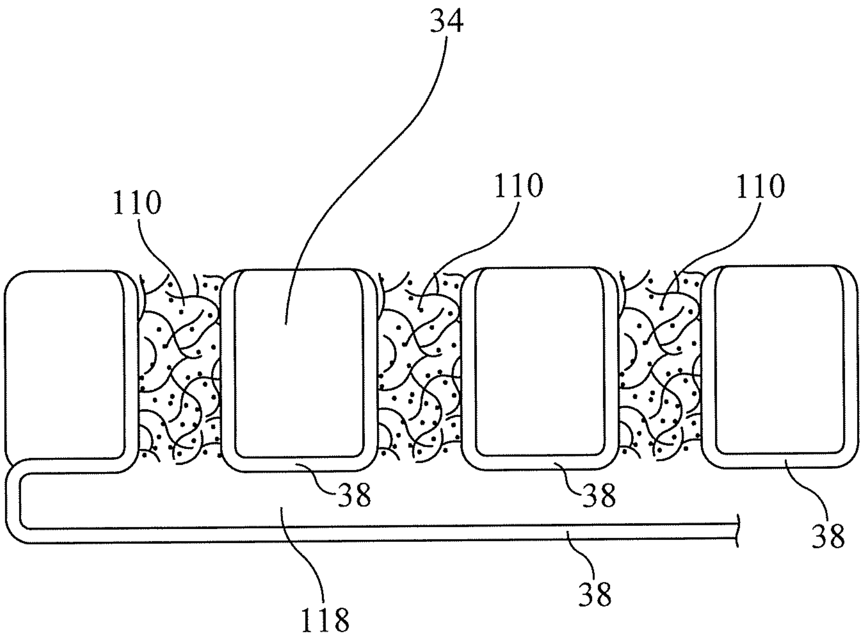
FIG. 13 is a view of a mattress architecture similar to that of FIGS. 12A, 12B and 12C in which the leak barrier forms a reservoir at the bottom of the phase changeable component.

FIG. 13 shows an embodiment in which the leak barrier 38 circumscribes each pedestal 110 and forms a common reservoir 118 at the bottom of the phase changeable component.

Figure 14:
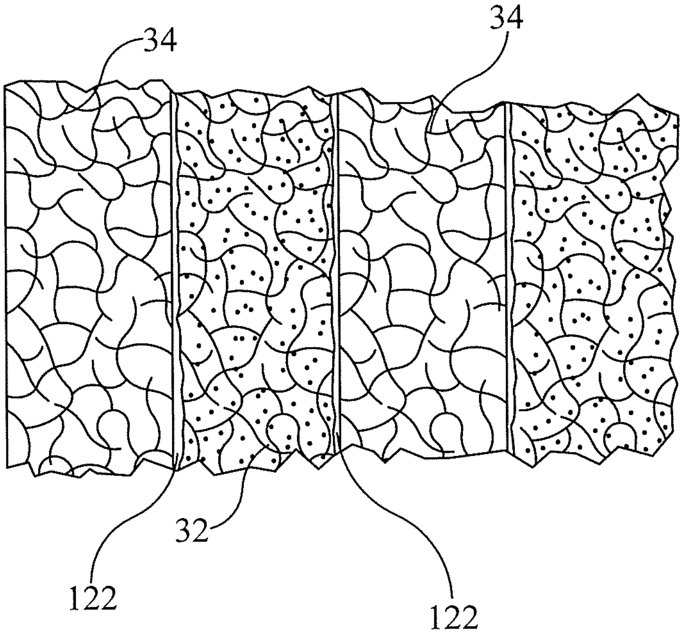
FIG. 14 is a cross sectional view of a mattress architecture comprised of a single phase component and a phase changeable component which are vertically coextensive with each other, and which includes a hydrophobic region in the vicinity of each pedestal.

Referring to FIG. 14, in lieu of a containment barrier as illustrated in FIGS. 12A-12C above, the foam of the single phase layer can be a hydrophobic foam, or can have a hydrophobic region 122 at least in the vicinity of each pedestal as seen in FIG. 14, in order to discourage wax migration into the single phase layer. In addition the foam of the phase changeable layer can be a hydrophilic foam.

The phase changeable layer, the thermal management system, or both may be adapted or arranged so that the firmness of the phase change layer is intentionally spatially nonuniform and/or intentionally temporally nonuniform. Unless specified otherwise, spatially nonuniform firmness means intentional spatially nonuniform firmness at steady state conditions as distinct from spatial firmness nonuniformity that might arise transiently as heat flows from or to the phase changeable component during a transition between two steady state thermal conditions. Unless specified otherwise temporally nonuniformity firmness means an intentional time varying firmness as distinct from firmness transients that might arise as heat flows from or to the phase changeable component during a transition between two steady state thermal conditions.

Figure 15:
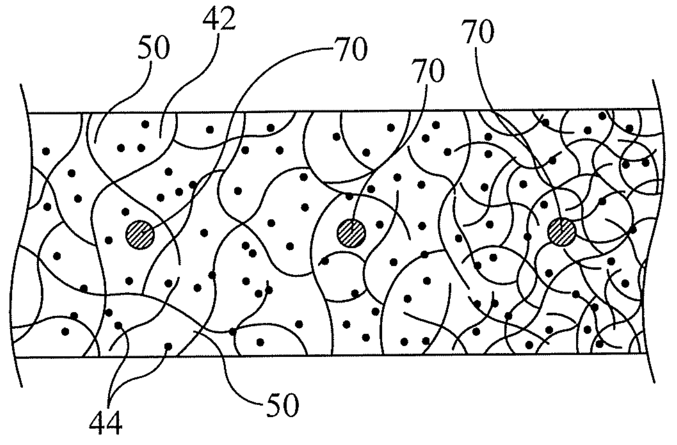
FIG. 15 is view of a portion of a phase changeable component in which the phase changeable component itself is arranged to achieve spatially nonuniform firmness.

FIG. 15 is an example of arranging a phase changeable layer to achieve spatially nonuniform firmness. The illustrated phase changeable layer comprises a reticulated backbone (strands 50) infused with wax 44 and threaded with wire heating elements 70. The strands 50 of the reticulated material are relatively loosely packed at the left side of the illustration (lower strand count per unit volume) and progressively more tightly packed (higher strand count per unit volume) as one moves to the right side of the illustration. When the wax is in its solid phase there is no intentional spatial nonuniformity of firmness because the firmness of the phase changeable layer is the firmness of the wax, and is unaffected by the density of the reticulated material. When the wax is heated and melts the phase changeable component exhibits a firmness which increases from left to right due to the increased strand count of the backbone. Assuming the heating of the wax is spatially uniform, the illustrated phase changeable layer is nondynamic in the sense that once the wax melts the spatial distribution of firmness is governed by the backbone strand density and cannot be altered by a user input.

Figure 16:
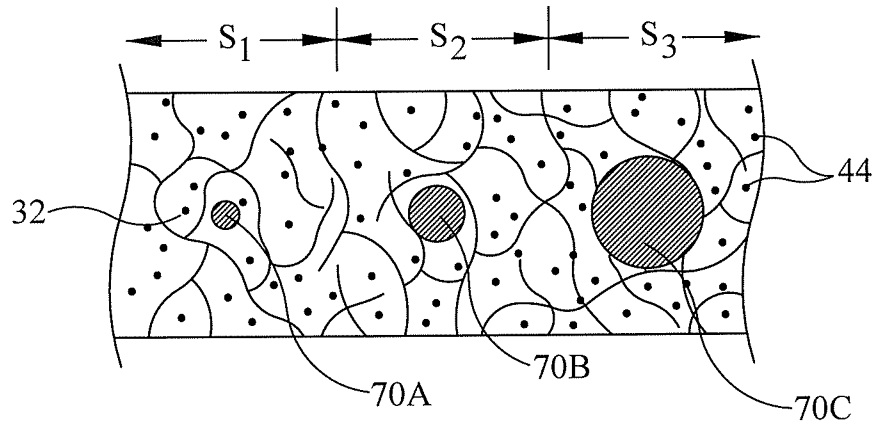
FIGS. 16-17 are views of a portion of a phase changeable component showing two ways of arranging the thermal management system to achieve spatially nonuniform firmness of the phase changeable component.

FIG. 16 is an example of arranging the thermal management system to achieve spatially nonuniform firmness. The illustrated phase changeable layer comprises a reticulated backbone (strands 50) infused with wax 44 and threaded with wire heating elements 70A, 70B, 70C each having a different electrical resistance $R_1$, $R_2$, $R_3$ such that $R_1>R_2>R_3$ (smaller diameter in the illustration signifies greater resistance). The strands 50 of the reticulated material are packed spatially uniformly. If the magnitude of electrical current is the same through each wire, wire 70A will introduce the most heat into the phase changeable layer and wire 70C will introduce the least. If, for example, the wax melts at 110 degrees and the heating wires 70A, 70B, 70C heat their surroundings to 120, 108 and 90 degrees, region $S_1$ of the layer will become soft, and region $S_3$ will remain firm. To the extent that the wax in region $S_2$ becomes soft but does not melt, that region may exhibit an intermediate firmness, greater than the firmness of $S_1$ but less than that of $S_3$. If the electrical current through all the wires is constant, the phase changeable layer is nondynamic in the sense that the spatial distribution of firmness is governed by the constant current. Dynamic performance can be introduced by providing a controller to vary the electrical current as a function of time through wires 70A, 70B and 70C.

Figure 17:
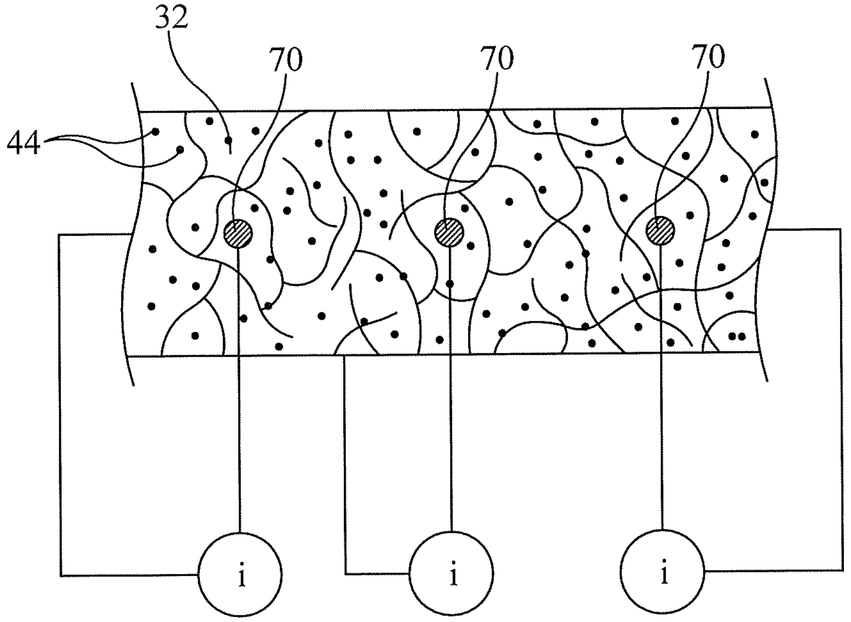

FIG. 17 is another example of arranging the thermal management system to achieve spatially nonuniform firmness. The illustrated phase changeable layer 32 comprises a reticulated backbone (strands 50) infused with wax 44 and threaded with wire heating elements 70 each having the same electrical resistance. The strands 50 of the reticulated material are packed spatially uniformly. Each of the illustrated wire heating elements is connected to a current source. If the electrical current is of the same constant magnitude in each wire, the layer will exhibit spatially uniform, time invariant firmness. If the current is changed to different constant values in each wire (including the limit case of no current), the firmness of the phase changeable layer can be made spatially nonuniform as in the example of FIG. 16. If the current is regulated so that it is the same in each wire but varies over time, the firmness of the phase changeable layer can be made temporally nonuniform.

The foregoing examples of ways that the firmness of the phase changeable layer can be made spatially and/or temporally nonuniform are not exhaustive.

In the examples of FIGS. 15-17 the spatial nonuniformity is one dimensional (left to right). In general, and irrespective of how the nonuniformity is achieved, the firmness can be made nonuniform in three directions—longitudinal, lateral and vertical or in fewer than all three directions.

FIGS. 18-23B are plan views showing various practical applications of a mattress having a phase changeable component. Although FIGS. 18-23B show only the phase changeable component 32, the practical applications would be equally valid if the optional single phase component were present.

Figure 18:
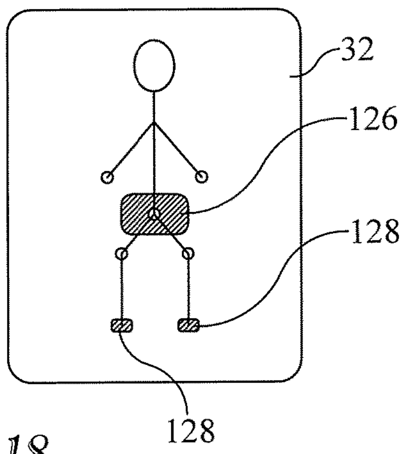
FIGS. 18, 19A, 19B, 20, 21A, 21B, 22A, 22B, 23A, and 23B are views showing various practical applications of a phase changeable component in a mattress.

FIG. 18 shows the phase changeable component being relatively soft in the vicinity of two anatomical regions susceptible to pressure ulcers, the patient's buttocks and sacrum (continuous region 126) and the patient's heels (discontinuous region 128). The softness can be different in each of the soft regions 126, 128.

Figure 19A:
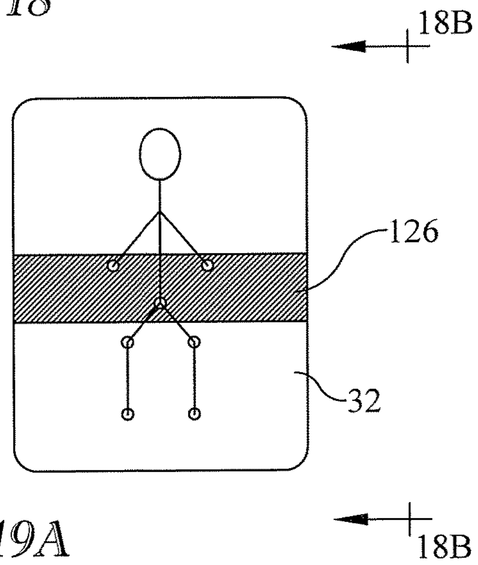
Figure 19B:
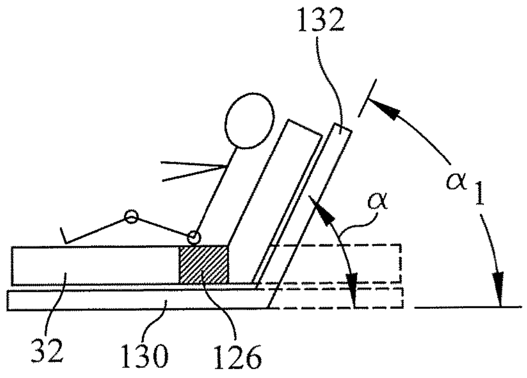

FIGS. 19A and 19B show the phase changeable component supported by a bed frame 130. Bed frame 130 includes an upper body section 132 which is orientation adjustable through angle α. The mattress bends to mimic the orientation of the upper body section. When the upper body section is at a flat (0 degree) orientation (phantom lines) the phase changeable component has a specified softness or firmness in region 126, which is the vicinity of the patient's buttocks. When the upper body section is rotated to a greater angle (solid lines) region 126 is made softer or firmer. One reason to make region 126 softer with increasing α is that as α increases, more of the patient's weight bears on section 126. As a result, the pressure exerted on the patient's buttocks increases, which increases the risk of pressure ulcer development. Accordingly, the embodiment of FIGS. 19A-19B can address both the inherent susceptibility of the patient's buttocks and sacral region to the development pressure ulcers (as in the embodiment of FIG. 18) as well as any additional susceptibility arising from the rotation of the upper body section of the frame. One reason to make region 126 firmer with increasing α is that as α increases the increased patient weight on region 126 increases the likelihood that the patient will bottom out. The difference in lateral extent of regions 126 in FIGS. 18 and 19 is a matter of design choice.

Figure 20:
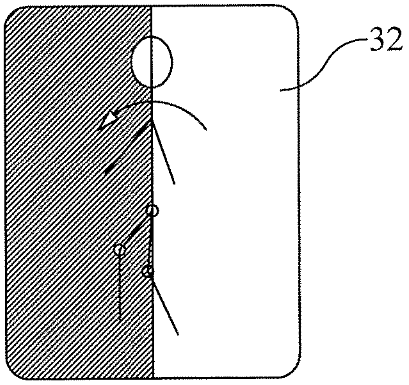

FIG. 20 shows the mattress with the right half of the phase changeable component in its soft state and the left half in its firm state (right and left are taken from the perspective of a supine patient). Such a configuration may help the nursing staff turn the patient from supine to prone or vice versa, or turn the patient partially, for example to conduct an examination of the patient's back. The capability to soften the phase changeable component is present on both the left and right sides in order to allow turning in either direction.

Figure 21A:
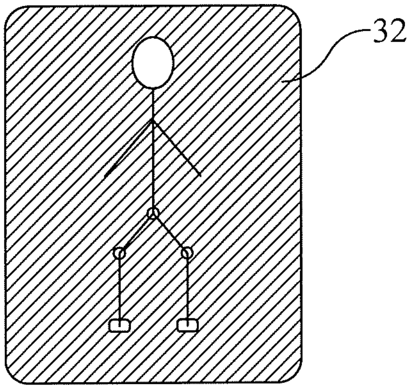
Figure 21B:
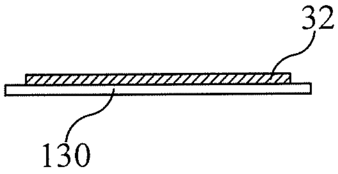

FIGS. 21A-21B show the mattress with the phase changeable component in its soft state everywhere, and to the maximum degree possible, so that the occupant "bottoms out" on the rigid frame 130. Ordinarily it is undesirable to allow the patient to bottom out on the frame. However temporary bottoming out may be desirable to permit effective application of cardiopulmonary resuscitation (CPR).

Figure 22A:
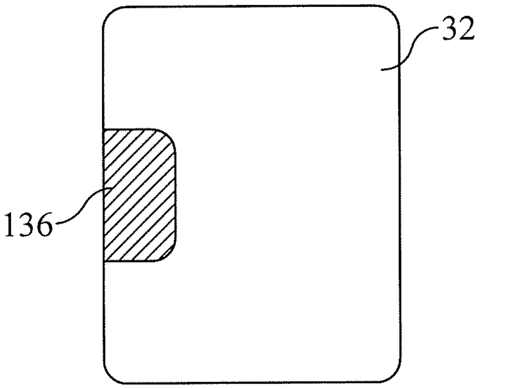
Figure 22B:
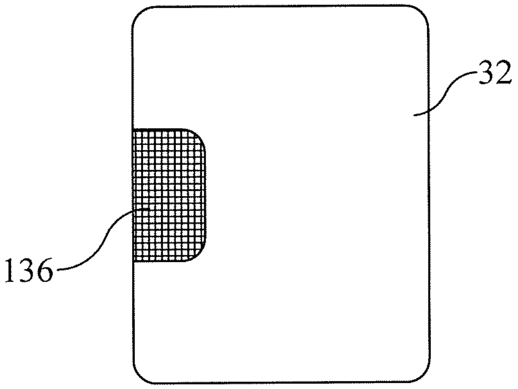

FIG. 22A shows the mattress in which a region 136 of the phase changeable component is in its soft state and the rest of the phase changeable component is in its firm state. FIG. 22B shows the mattress in which region 136 of the phase changeable component is in its firm state and the rest of the phase changeable component is in its soft state. The reduced or increased firmness may be desirable for a side sitting patient or for facilitating patient egress from the mattress or ingress onto the mattress.

Figure 23A:
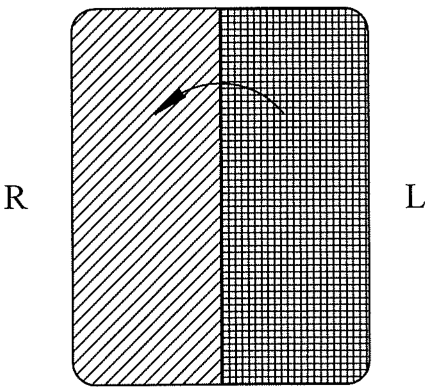
Figure 23B:
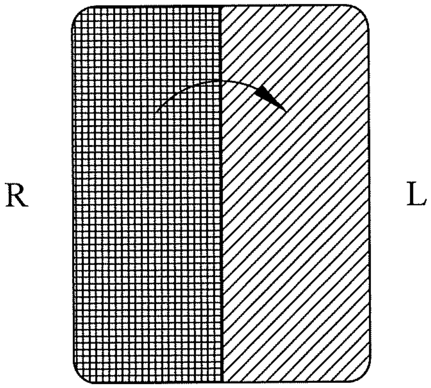

FIG. 23A shows the phase changeable component at a time $t_1$. At time $t_1$ the right side of the phase changeable component is in a relatively soft state and the left side is in a relatively firm state. FIG. 23B shows the phase changeable component at a time $t_2$. At time $t_2$ the left side of the phase changeable component is in its relatively soft state and the right side is in its relatively firm state. The ability to soften and stiffen opposite sides of the mattress out of phase with each other (one side firm, the other soft) may enable the application of a rotation therapy which is any therapy that calls for the patient to be gently rocked from side to side.

Figure 24:
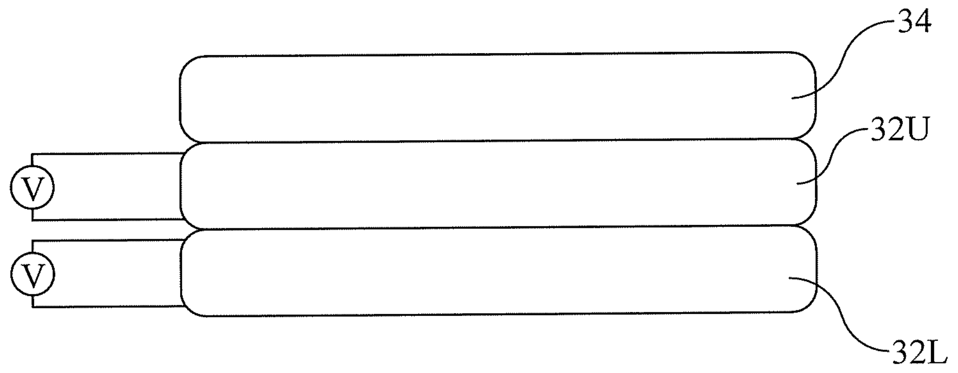
FIG. 24 is a view of a mattress having a single phase component, an upper phase changeable component, and a lower phase changeable component.

FIG. 24 shows a mattress having a single phase component 34, an upper phase changeable component 32U and a lower phase changeable component 32L. The upper phase changeable component 32U may be placed in a firm state having a firmness $F_{UH}$ and in a soft or more compliant state having a firmness $F_{US}$. The lower phase changeable component 32L may be placed in a firm state having a firmness $F_{LH}$ and in a soft or more compliant state having a firmness $F_{LS}$. As noted previously it may be possible to also achieve states of intermediate firmness between the firm state and the soft state for each component 32L, 32U. Phase changeable components 32L, 32U act like springs in series and therefore enable attainment of degrees of firmness or softness not achievable with only one phase changeable component.

Figure 25:
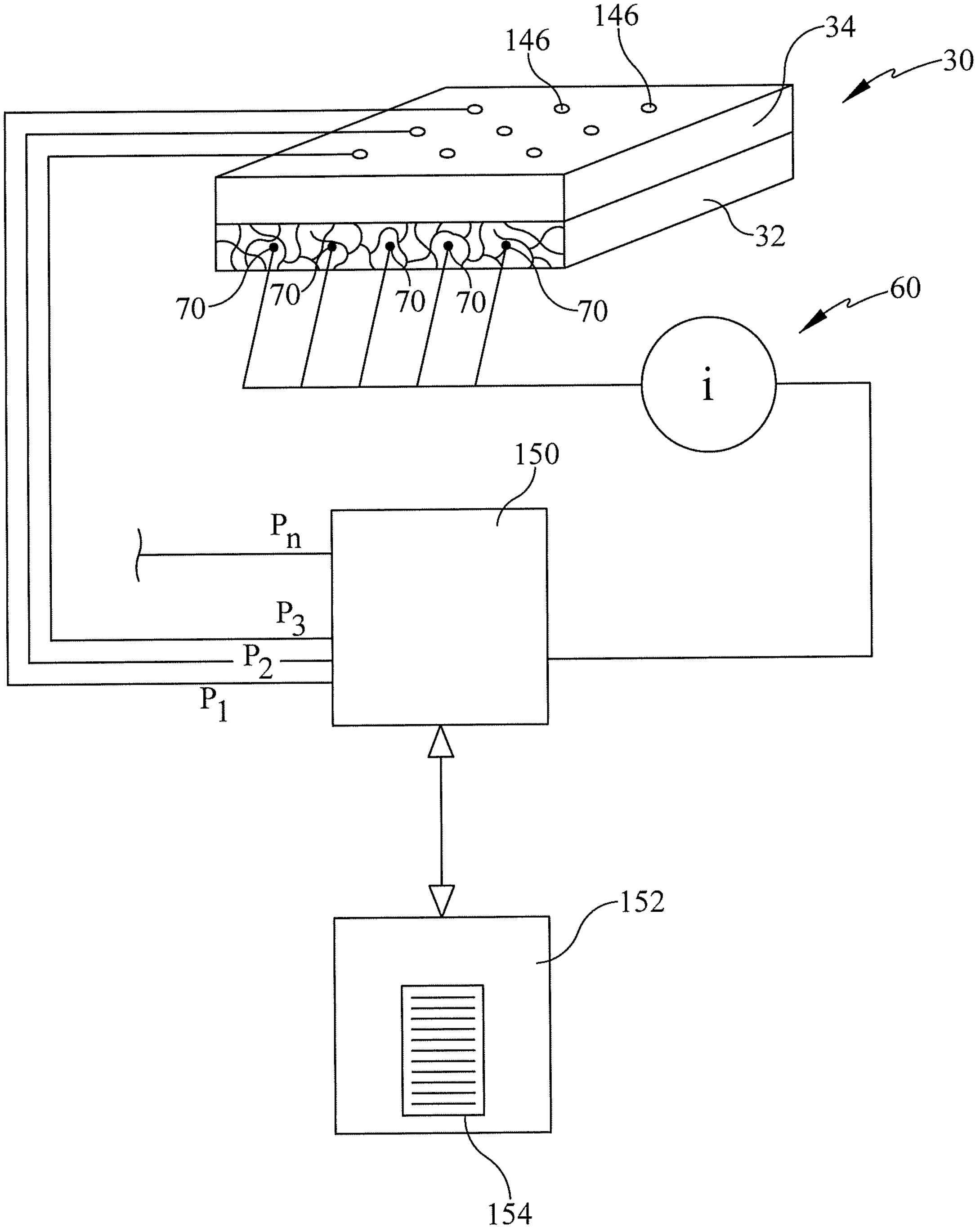
FIG. 25 is a schematic view of a closed loop system for regulating operation of a thermal management system to adjust the firmness of a phase changeable component of a mattress as a function of a sensed parameter.

FIG. 25 shows a closed loop system including a mattress comprised of a single phase component 34, a phase changeable component 32, and a thermal management system 60 represented by a current source and resistance heating wires 70. The mattress also includes parameter sensors or transducers 146 to sense one or more parameters associated with the patient. The sensors are illustrated as being on the top surface of the single phase component, but may be located at other places, including between the single phase component and the phase changeable component, in the interior of the single phase component, or in the interior of the phase changeable component. In one embodiment the sensors are pressure sensors and the parameter is pressure applied to the mattress by the patient. In another embodiment the sensors are force sensors and the parameter is force applied to the mattress by the patient. In yet another embodiment, patient weight and the orientation angle of the upper body section are used as an indicator of patient weight exerted on the mattress or on a portion thereof. The system also includes a controller or processor 150, and a memory 152 whose contents include instructions 154 which are executable by the processor or which can be put into a form executable by the processor.

In operation the processor receives parameter signals (e.g. $P_1, P_2, \ldots P_n$) and executes instructions 154 to assess whether the signals indicate that the patient is receiving adequate or inadequate support from the mattress. If the support is inadequate, the processor issues one or more command signals in an effort to regulate the operation of the thermal management system to correct the inadequacy.

More specifically the system regulates operation of the thermal management system to adjust the firmness of the phase changeable component as a function of the sensed parameter in comparison to a desired value of the sensed parameter. In one embodiment the parameter is a parameter that indicates a force attributable to the patient's weight. In another embodiment the parameter is a parameter that indicates the patient's morphology. In another embodiment the parameter is a parameter that indicates the patient's spatial distribution on the mattress. Spatial distribution refers to, for example, whether the patient is centered or off-center, lying prone or supine, stretched out or curled up, aligned with or skewed relative to the bed (e.g. sagittal plane approximately parallel to or not parallel to the edge of the mattress).

Irrespective of the parameter sensed, the processor is adapted to regulate operation of the thermal management system to control firmness of the phase changeable component as a function of the sensed parameter in comparison to a desired value of the sensed parameter.

The instructions adapt the processor to operate the thermal management system in a way that will control the firmness of the mattress in order to optimize the pressure exerted on the occupant's body. Optimization of the exerted pressure means that no portion of the patient's body experiences pressure high enough to cause an unacceptable risk that the patient will develop pressure ulcers. The control may be exercised in such a way that the firmness of the phase changeable layer, and therefore of the mattress as a whole, is spatially nonuniform, temporally nonuniform, or both.

Figure 26:
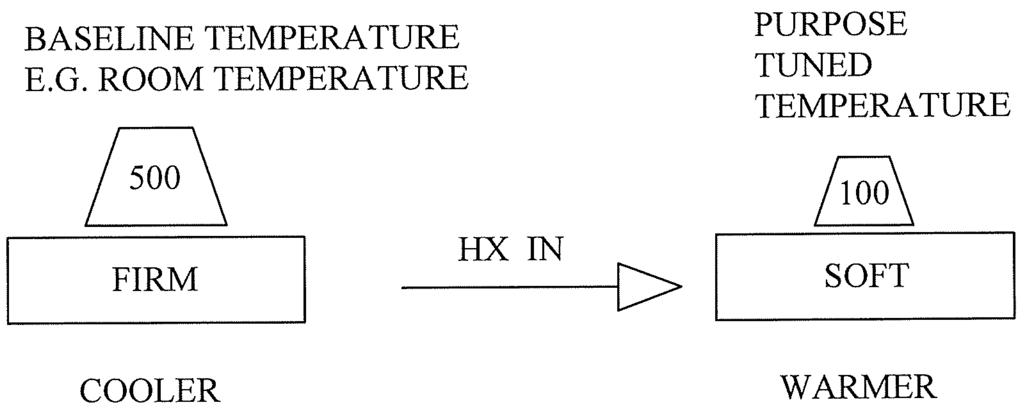
FIG. 26 is a diagram illustrating a method of operating a mattress in which the thermal management system includes only a heat supply system.

FIG. 26 illustrates a method of operation of a mattress in which the thermal management system comprises only a heat supply system, e.g. as seen in FIG. 1.

According to this example the wax of the phase changeable layer is solid at a baseline temperature, for example room temperature. The baseline mattress is therefore suitable for a heavy patient or for a range of heavier patient weights as signified by the 500 pound (227 kg) weight symbol. In order to accommodate a lighter patient or a range of lighter patient weights, as signified by the 100 pound (45 kg) weight symbol, the heat supply system is operated to raise the temperature of the wax to a temperature "purpose tuned" for the lighter patient or range of lighter patient weights. The purpose tuned temperature is the temperature at which the wax melts or the temperature required to achieve a softer intermediate state. The transition of the phase changeable layer from firm to soft can take place relatively quickly and can occur whether or not a patient is occupying the mattress.

As already noted the reverse transition from firm to soft may require that the patient's weight be removed from the mattress, specifically from the phase changing component. The patient's weight can be completely removed from the mattress. Alternatively the patient's weight can be shifted to, say, the left side of the mattress to allow the right side to transition from softer to firmer, followed by shifting the patient's weight to the right side of the mattress to allow the left side to transition from softer to firmer. Because the thermal management system includes a heat supply system but no heat withdrawal system, the heat withdrawal will be unforced. As a result the soft-to-firm transition and will likely take more time than the firm-to-soft transition.

Figure 27:
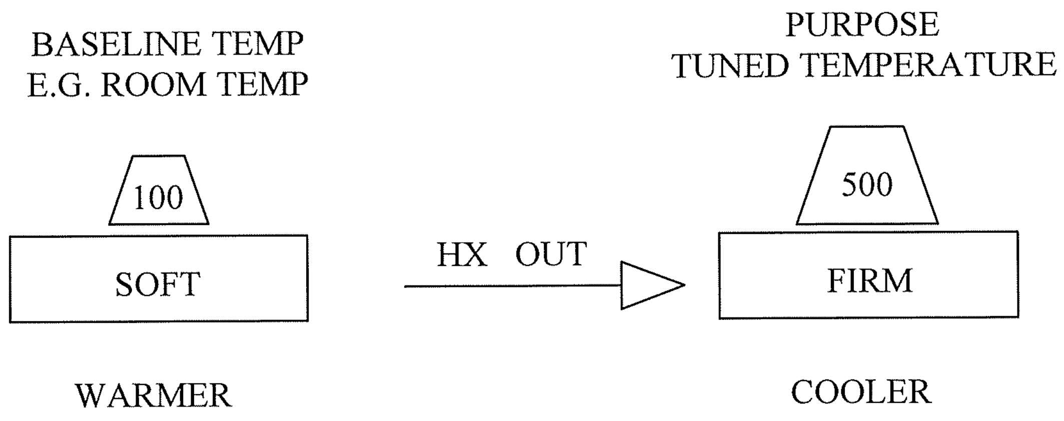
FIG. 27 is a diagram illustrating a method of operating a mattress in which the thermal management system includes only a heat withdrawal system.

FIG. 27 illustrates a method of operation of a mattress in which the thermal management system comprises only a heat withdrawal system, e.g. as seen in FIG. 5. The phase changeable layer includes a wax which is liquid at a baseline temperature, for example room temperature. The baseline mattress is therefore suitable for a light patient or for a range of lighter patient weights as signified by the 100 pound (45 kg) weight symbol. In order to accommodate a heavier patient or a range of heavier patient weights, as signified by the 500 pound (227 kg) weight symbol, the heat withdrawal system is operated to lower the temperature of the wax to a temperature purpose tuned for the heavier patient or range of heavier patient weights. The purpose tuned temperature is the temperature at which the wax becomes solid or at least semi-rigid (solid phase but less firm than completely solidified wax). If necessary, the patient's weight can be completely removed from the phase changeable component or can be shifted from place to place to enable the liquid-to-solid transition. Because the thermal management system includes a heat withdrawal system but no heat supply system, heat transfer into the phase changeable layer will be unforced. As a result the firm-to-soft transition will likely take more time than the soft-to-firm transition.

Figure 28:
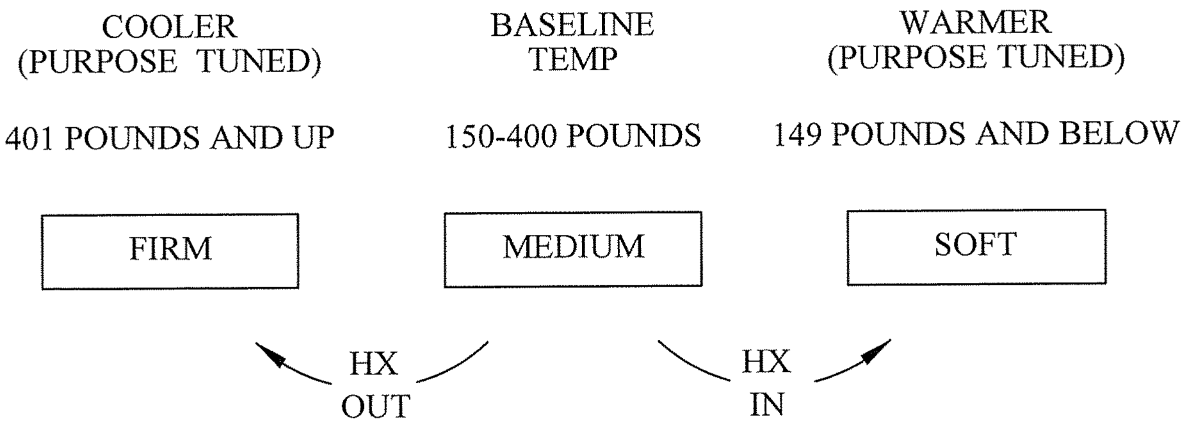
FIG. 28 is a diagram illustrating a method of operating a mattress in which the thermal management system includes both a heat supply system and a heat withdrawal system.

FIG. 28 illustrates a method of operation of a mattress constructed with the thermal management system of FIG. 6, i.e. one that includes both a heat supply system and a heat withdrawal system. The phase changeable layer includes a wax which is semi-firm at a baseline temperature, for example room temperature. The baseline mattress is therefore suitable for a mid-weight patient or for a range of mid-weight patients, for example in the 150 to 400 pound (68 to 182 kg) range. In order to accommodate a heavier patient or a range of heavier patient weights, for example patients weighing more than 400 pounds, the heat withdrawal system is operated to lower the temperature of the wax to a purpose tuned cooler temperature at which the wax becomes solid, or at least more rigid. As already noted it may be necessary to unload the phase changeable component in order to effect the change from softer to firmer. In order to accommodate a lighter patient or a range of lighter patient weights, for example patients weighing less than 150 pounds, the heat supply system is operated to raise the temperature of the wax to a purpose tuned warmer temperature at which the wax becomes liquid or at least less rigid. If a large segment of the expected patient population falls within the mid-weight range (e.g. 80% of the population) it will be necessary to energize the thermal management system only for the smaller segments of the population that fall in the light weight range or heavy weight range. Over time this could result in noteworthy savings on the energy required to operate the thermal management system.

Although this disclosure refers to specific embodiments, it will be understood by those skilled in the art that various changes in form and detail may be made without departing from the subject matter set forth in the accompanying claims.

I claim:

1. A mattress comprising:

a first, phase changeable component which includes separated 2D lattices with a spring element extending between the lattices; and a thermal management system adapted to control the temperature of the phase changeable component thereby changing firmness of the mattress.

2. The mattress of claim 1 wherein the spring element is an arcuate element.

3. The mattress of claim 1 wherein the spring element is a backbone of the phase changeable component, and the phase changeable component also includes a thermally active element which is adapted to transition from a firmer state to a softer state with increasing temperature, and from the softer state to the firmer state with decreasing temperature.

4. The mattress of claim 1 wherein the spring element is a backbone of the phase changeable component, and the phase changeable component also includes a thermally active element which is adapted to transition from a solid state to a liquid state with increasing temperature and from the liquid state to the solid state with decreasing temperature.

5. The mattress of claim 4 wherein the thermally active element is wax which coats the spring element when the wax is in its solid state.

6. The mattress of claim 5 wherein the wax at least partially coats the lattices when the wax is in the solid state.

7. The mattress of claim 1 including a second, single phase component.

8. The mattress of claim 7 wherein the single phase component is a single phase layer and the phase changeable component is a phase changeable layer.

9. The mattress of claim 7 wherein the single phase component and the phase changeable component are at least partly vertically coextensive.

10. The mattress of claim 7 wherein the single phase component and the phase changeable component are arranged so that when the mattress is used as intended by its manufacturer or designer the foam layer is vertically above the phase changeable layer.

11. The mattress of claim 10 including at least one of:

A) a thermal barrier between the single phase layer and the phase changeable layer, and B) a thermal conductor between the single phase layer and the phase changeable layer;

wherein when the mattress includes both the thermal barrier and the thermal conductor, the thermal conductor is closer to the single phase layer and the thermal barrier is closer to the phase changeable layer.

12. The mattress of claim 1 wherein the thermal management system is one or both of A) a heat supply system adapted to supply heat to the phase changeable component and B) a heat withdrawal system adapted to withdraw heat from the phase changeable component.

13. The mattress of claim 12 wherein the heat supply system is an electrical resistive heating element, and the heat withdrawal system is a Peltier device.

14. The mattress of claim 1 wherein one or both of the phase changeable component and the thermal management system are adapted to cause the firmness of the phase changeable component to be spatially nonuniform.

15. The mattress of claim 14 wherein the mattress extends in longitudinal, lateral and vertical directions and one or both of the phase changeable layer and the thermal management system are adapted to cause the firmness of the phase changeable layer to be nonuniform in fewer than all of the longitudinal, lateral and vertical directions.

16. The mattress of claim 1 wherein one or both of the phase changeable layer and the thermal management system are adapted to cause the firmness of the phase changeable layer to be temporally nonuniform.

17. The mattress of claim 1 including:

a sensor adapted to sense a parameter associated with an occupant of the mattress; and a processor adapted to regulate operation of the thermal management system to control firmness of the phase changeable component as a function of the sensed parameter.

18. The mattress of claim 17 wherein the parameter is at least one of pressure and force.

19. The mattress of claim 17 wherein the parameter is related to at least one of:

A) occupant weight;

B) occupant morphology; and

C) occupant distribution on the mattress.

20. The mattress of claim 17 wherein the processor is adapted to regulate operation of the thermal management system to control the firmness of the phase changeable component such that the firmness is at least one of:

A) spatially nonuniform, and

B) temporally nonuniform.

* * * * *